(12) United States Patent
Wu et al.

(10) Patent No.: US 9,855,099 B2
(45) Date of Patent: Jan. 2, 2018

(54) LASER DEVICES UTILIZING ALEXANDRITE LASER OPERATING AT OR NEAR ITS GAIN PEAK AS SHORTER-WAVELENGTH PUMPING SOURCES AND METHODS OF USE THEREOF

(71) Applicant: Light Age, Inc., Somerset, NJ (US)

(72) Inventors: Chunbai Wu, New Brunswick, NJ (US); Donald F. Heller, Somerset, NJ (US)

(73) Assignee: Light Age, Inc., Somerset, NJ (US)

( * ) Notice: Subject to any disclaimer, the term of this patent is extended or adjusted under 35 U.S.C. 154(b) by 0 days.

(21) Appl. No.: 15/165,475

(22) Filed: May 26, 2016

(65) Prior Publication Data

US 2016/0270849 A1    Sep. 22, 2016

Related U.S. Application Data

(63) Continuation of application No. 14/216,387, filed on Mar. 17, 2014, now Pat. No. 9,351,793.

(Continued)

(51) Int. Cl.
*A61B 18/20* (2006.01)
*H01S 3/16* (2006.01)
*H01S 3/04* (2006.01)
*H01S 3/06* (2006.01)
*A61B 18/00* (2006.01)
(Continued)

(52) U.S. Cl.
CPC .......... *A61B 18/203* (2013.01); *H01S 3/1616* (2013.01); *A61B 2018/00452* (2013.01); *A61B 2018/2035* (2013.01); *A61B 2018/2065* (2013.01); *H01S 3/005* (2013.01); *H01S 3/0007* (2013.01); *H01S 3/025* (2013.01); *H01S 3/042* (2013.01); *H01S 3/0404* (2013.01);
(Continued)

(58) Field of Classification Search
CPC ........ H01S 3/1616; H01S 3/025; H01S 3/042; H01S 3/005; H01S 3/1643; H01S 3/0007; H01S 3/094038; H01S 3/0405; H01S 3/061
See application file for complete search history.

(56) References Cited

U.S. PATENT DOCUMENTS

| 9,351,793 B2* | 5/2016 | Wu ...................... A61B 18/203 |
| 2007/0291800 A1* | 12/2007 | Finot .................... G02B 6/4201 372/20 |
| 2016/0045265 A1* | 2/2016 | Bhawalkar ........... A61B 18/203 606/9 |

* cited by examiner

*Primary Examiner* — Dung Nguyen
(74) *Attorney, Agent, or Firm* — Greenberg Traurig, LLP

(57) ABSTRACT

In some embodiments, the instant invention provides for a system that includes at least the following components: (i) an Alexandrite laser pumping subsystem; where the Alexandrite laser pumping subsystem is configured to: 1) produce wavelengths between 700 and 820 nm, and 2) produce a pump pulse having: i) a duration between 1 to 10 milliseconds, and ii) an energy measuring up to 100 Joules; where the Alexandrite laser pumping subsystem includes: 1) an optical fiber, and 2) a Lens system, (ii) a Thulium doped Yttrium Aluminum Garnet (Tm:YAG) laser subsystem; where the Tm:YAG laser subsystem includes: 1) a Tm:YAG gain medium, 2) a rod heat sink, and 3) at least one cooling device, (iii) a wavelength selecting device, where the wavelength selecting device is configured to deliver a wavelength between 1.75 microns to 2.1 microns; and where the system is configured to produce a high energy conversion efficiency.

20 Claims, 13 Drawing Sheets

Related U.S. Application Data

(60) Provisional application No. 61/883,716, filed on Sep. 27, 2013, provisional application No. 61/791,340, filed on Mar. 15, 2013.

(51) Int. Cl.
  *H01S 3/094* (2006.01)
  *H01S 3/00* (2006.01)
  *H01S 3/02* (2006.01)
  *H01S 3/042* (2006.01)

(52) U.S. Cl.
  CPC ............ *H01S 3/0405* (2013.01); *H01S 3/061* (2013.01); *H01S 3/094038* (2013.01); *H01S 3/1643* (2013.01)

LASER DEVICES UTILIZING ALEXANDRITE LASER OPERATING AT OR NEAR ITS GAIN PEAK AS SHORTER-WAVELENGTH PUMPING SOURCES AND METHODS OF USE THEREOF

RELATED APPLICATIONS

This application is a continuation of U.S. patent application Ser. No. 14/216,387, entitled "LASER DEVICES UTILIZING ALEXANDRITE LASER OPERATING AT OR NEAR ITS GAIN PEAK AS SHORTER-WAVELENGTH PUMPING SOURCES AND METHODS OF USE THEREOF," filed Mar. 17, 2014, which claims the priority of U.S. provisional application Ser. No. 61/791,340, entitled "LASER DEVICES UTILIZING ALEXANDRITE LASER AS PUMPING SOURCE AND METHODS OF USE THEREOF," filed Mar. 15, 2013; and U.S. provisional application Ser. No. 61/883,716, entitled "LASER DEVICES UTILIZING ALEXANDRITE LASER OPERATING AT OR NEAR ITS GAIN PEAK AS SHORTER-WAVELENGTH PUMPING SOURCES AND METHODS OF USE THEREOF," filed Sep. 27, 2013, which are incorporated herein by reference in their entireties for all purposes.

FIELD OF THE INVENTION

The embodiments of the present invention relate to laser devices utilizing Alexandrite laser operating at or near its gain peak as shorter-wavelength pumping sources and methods of use thereof.

BACKGROUND OF INVENTION

In some instances, Alexandrite laser systems, which utilize an alexandrite crystal as a gain medium, are typically utilized in Dermatology, laser machining, and remote sensing technology. In some instances, pump sources for the alexandrite crystal in the Alexandrite laser systems can, typically, be selected from the group consisting of, but is not limited to: a flashlamp, a laser diode, a mercury arc, and other similarly suitable source. In some instances, the Alexandrite laser systems are typically tuned to an operation wavelength in the range of, e.g., 700 to 820 nm.

BRIEF SUMMARY OF INVENTION

In some embodiments, the instant invention provides for a system that includes at least the following components: (i) an Alexandrite laser pumping subsystem; where the Alexandrite laser pumping subsystem is configured to: 1) produce wavelengths between 700 and 820 nm, and 2) produce a pump pulse having: i) a duration between 1 to 10 milliseconds, and ii) an energy measuring up to 100 Joules; where the Alexandrite laser pumping subsystem includes: 1) at least one optical fiber, and 2) at least one Lens system, where the at least one optical fiber is configured to deliver an Alexandrite output beam of an Alexandrite gain medium into the at least one Lens system; (ii) a Thulium doped Yttrium Aluminum Garnet (Tm:YAG) laser subsystem; where the Tm:YAG laser subsystem includes: 1) a Tm:YAG gain medium; where a Tm:YAG gain medium of the Tm:YAG laser subsystem is optically pumped by the Alexandrite laser pumping subsystem; where the Tm:YAG gain medium is doped with Tm3+ ions to a concentration of between 1% and 50% Tm3+ ions; and where the at least one Lens system is configured to collimate the Alexandrite output beam from the at least one optical fiber to a size that is smaller than a diameter of the Tm:YAG gain medium; 2) a rod heat sink, where the rod heat sink encases the Tm:YAG gain medium; and 3) at least one cooling device, where the at least one cooling device is configured to stabilize the temperature of the Tm:YAG gain medium; (iii) a wavelength selecting device, where the wavelength selecting device is configured to deliver a wavelength between 1.75 microns to 2.1 microns; and where the system is configured to produce a high energy conversion efficiency at: 1) multi-Joule-Level pulse energies and 2) multi-Watt Level average powers.

In some embodiments, the Alexandrite laser pumping subsystem further includes: (i) a fiber input adapter and (ii) at least one input lens, where the at least one input lens is encased in the fiber input adapter.

In some embodiments, the Tm:YAG laser subsystem further includes: (i) a rod heat sink, where the rod heat sink is directly contacting the fiber input adapter; (ii) a high reflector, where the high reflector is encased in the fiber input adapter and is optically contacting with the at least one input lens; (iii) at least one output coupler, where the at least one output coupler is directly contacting the heat rod sink; (iv) a dichroic glass, where the dichroic glass is optically contacting the at least one output coupler; and (v) at least one output lens, where the at least one output lens is optically contacting the dichroic glass.

In some embodiments, the system further includes a micro-lens array, where the micro-lens array is configured to form a pattern, where the pattern is determined by a pitch and a focal length of the micro-lens array; and where the micro-lens array is optically contacting the at least one output lens.

In some embodiments, the system further includes: a compact Thulium ion-based wavelength convertor configured to fit into a handpiece, where the handpiece includes: (i) an air input adapter, (ii) a fiber input adapter, (iii) an air integrator, (iv) an air output/air guide, and (v) a Tm:YAG output.

In some embodiments, the Alexandrite laser pumping subsystem is configured to use cold airflow to remove heat from the Tm:YAG laser subsystem.

In some embodiments, the system is utilized for a dermatologic surgery, where the dermatologic surgery is selected from the group consisting of: fractional resurfacing of facial actinic keratosis, treatment of non-facial photo damage, treatment of actinic cheilitis, treatment of macular seborrheic keratosis, treatment of melisma cheilitis, and treatment by removal of facial wrinkles.

In some embodiments, the Alexandrite output beam measuring between 750-760 nm and an output energy measuring between 1 ms-10 ms durations results in a Tm:YAG output measuring between 1 J-10 J at 2 microns.

In some embodiments, the Alexandrite output beam is configured to be delivered at a wavelength of 755 nm.

In some embodiments, the micro-lens array is configured to generate a spot size of about 360 microns and a fill factor of about 10%.

In some embodiments, the Tm:YAG gain medium is in a form of a rod measuring 5 mm in diameter and 60 mm in length.

In some embodiments, the system further includes: a cavity configured to encase at least one pump mirror, the Tm:YAG gain medium, and the at least one output coupler.

In some embodiments, the at least one pump mirror is configured to achieve at least 80% reflectivity for 1.85-2.1 um.

In some embodiments, the instant invention provides for a method that includes at least the following steps: (i) utilizing an Alexandrite laser pumping subsystem; where the Alexandrite laser pumping subsystem is configured to: 1) produce wavelengths between 700 and 820 nm, and 2) produce a pump pulse having: i) a duration between 1 to 10 milliseconds, and ii) an energy measuring up to 100 Joules; where the Alexandrite laser pumping subsystem includes: 1) at least one optical fiber, and 2) at least one Lens system, where the at least one optical fiber is configured to deliver an Alexandrite output beam of an Alexandrite gain medium into the at least one Lens system; (ii) utilizing a Thulium doped Yttrium Aluminum Garnet (Tm:YAG) laser subsystem; where the Tm:YAG laser subsystem includes: 1) a Tm:YAG gain medium; where a Tm:YAG gain medium of the Tm:YAG laser subsystem is optically pumped by the Alexandrite laser pumping subsystem; where the Tm:YAG gain medium is doped with Tm3+ ions to a concentration of between 1% and 50% Tm3+ ions; and where the at least one Lens system is configured to collimate the Alexandrite output beam from the at least one optical fiber to a size that is smaller than a diameter of the Tm:YAG gain medium; 2) a rod heat sink, where the rod heat sink encases the Tm:YAG gain medium; and 3) at least one cooling device, where the at least one cooling device is configured to stabilize the temperature of the Tm:YAG gain medium; (iii) utilizing a wavelength selecting device, where the wavelength selecting device is configured to deliver a wavelength between 1.75 microns to 2.1 microns; and where the system is configured to produce a high energy conversion efficiency at: 1) multi-Joule-Level pulse energies and 2) multi-Watt Level average powers.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
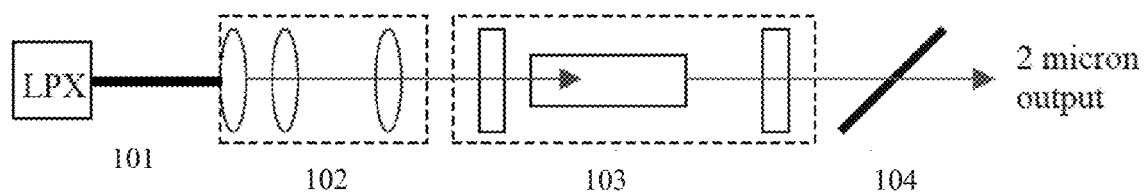
FIG. 1 illustrates some embodiments of the present invention.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION OF VARIOUS EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive. Any alterations and further modifications of the inventive feature illustrated herein, and any additional applications of the principles of the invention as illustrated herein, which would normally occur to one skilled in the relevant art and having possession of this disclosure, are to be considered within the scope of the invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the instant invention involves the laser devices utilizing Alexandrite laser pumping subsystems operating at or near its gain peak as pumping sources at wavelengths shorter than 800 nm. In some embodiments, the instant invention involves the laser devices utilizing the Alexandrite laser pumping subsystems operating at or near its gain peak as pumping sources at wavelengths shorter than 780 nm. In some embodiments, the instant invention involves the laser devices utilizing the Alexandrite laser pumping subsystems operating at or near its gain peak as pumping sources at wavelengths between, e.g., 700 and 820 nm. In some embodiments, the instant invention involves the laser devices utilizing the Alexandrite laser pumping subsystems operating at or near its gain peak as pumping sources at wavelengths between, e.g., 720 and 780 nm. In some embodiments, the instant invention involves the laser devices utilizing the Alexandrite laser pumping subsystems operating at or near its gain peak as pumping sources at wavelengths between, e.g., 750 and 765 nm. In some embodiments, the instant invention involves the laser devices utilizing the Alexandrite laser pumping subsystems operating at or near its gain peak as pumping sources at such wavelengths where the alexandrite crystal has maximum gain and where the Alexandrite laser pumping subsystems are under normal (non-tuned) operation.

In some embodiments, the instant invention involves the laser devices utilizing the Alexandrite laser pumping subsystems to pump a gain medium of Thulium doped Yttrium Aluminum Garnet (Tm:YAG).

In some embodiments, the instant invention involves the laser devices utilizing a q-switched Alexandrite pumping laser subsystems having nanosecond (ns) pulse durations which are less than a long-pulse (normal mode) alexandrite laser. In some embodiments, the pumped gain medium exhibits a switched peak (Q-Switching) or peaks having few µs or even sub µs output pulse durations. In some embodiments, the pumped gain medium exhibits a switched peak (Q-Switching) or peaks having output pulse durations in the order of, e.g., 10-100 ns.

In some embodiments, the instant invention involves the laser devices utilizing the Alexandrite pumping laser subsystems having the pump duration between, e.g., 1 to 3 milliseconds. In some embodiments, the instant invention involves the laser devices utilizing the Alexandrite pumping laser subsystems having the pump duration between, e.g., 1 to 5 milliseconds. In some embodiments, the instant invention involves the laser devices utilizing the Alexandrite pumping laser subsystems having the pump duration between, e.g., 1 to 10 milliseconds.

In some embodiments, the instant invention involves the laser devices utilizing an Alexandrite laser-pumped q-switched Tm:YAG laser employing a saturable absorber. In some embodiments, for example, the instant invention can utilize saturable absorbers like the one identified by Kuo, Yen-Kuang, and Yi-An Chang, "Numerical Study of Passive Q Switching of a Tm:YAG Laser with a Ho:YLF Solid-State Saturable Absorber," Applied Optics 42(2003): 1685-1691, whose the specific disclosures related to saturable absorbers are hereby incorporated herein by reference for such specific purposes. Specifically, the characteristics of the laser output depends on the initial population in the ground state of the Ho:YLF saturable absorber, the location of the saturable absorber, the pumping rate, the reflectivity of the output coupler, and the focal length of the focusing lens. With a typical laser configuration, a Q-switched laser pulse of >35 mJ in 30 ns can be obtained.

In some embodiments, the instant invention utilizes: (1) the disclosed pump wavelengths at or near, e.g., 750 to 755 nm and (2) the pump pulse energies up to 100 Joules used,—to achieve corresponding output energies, obtained in the µs and ms pulse duration regimes, without substantial surface and/or bulk damage to the Tm:YAG crystal.

In some embodiments, the instant invention involves the laser devices utilizing Alexandrite laser to pump a gain medium of co-doped Tm materials, such as Tm:Ho:YAG and other related materials including, but are not limited to, Tm containing YALO and ZBLAN hosts.

In some embodiments, the instant invention allows a high (≈20% optical-to-optical) energy conversion efficiency from, e.g., ≈755 nm to ≈2 µm at multi-Joule-level pulse energies and multi-Watt Level average powers.

In some embodiments, the inventive laser device of the instant invention are suitable for applications in cosmetic dermatology and/or other medical applications such as, but not limited to, using a compact Tm ion-based wavelength convertor that fits into a handpiece that can adapt into a medical Alexandrite laser system. In some embodiments, the inventive laser device of the instant invention utilize active cooling using cold airflow to remove heat from the Tm-ion laser material is generally required for continuous and stable high power operation.

Referring to FIG. 1 that illustrates an exemplary schematic representation of some embodiments of the instant invention. FIG. 1 illustrates that some embodiments of the instant invention include solid-state compact laser systems that utilize a gain medium of Thulium doped Yttrium Aluminium Garnet (Tm:YAG) in a form of an elongated object (e.g., rod, rectangular-shaped prism, etc.) which is optically pumped by the Alexandrite laser system(s). In some embodiments, the suitable Alexandrite lasers can include, but are not limited to, the following laser systems:

i) LP laser system: Light Age, Inc.'s Epicare-LP™ (Somerset, N.J.), the Alexandrite laser generating the light output at ~755 nm, with average power up to 65 Watts; pulse rate up to 3 Hz; and pulse duration from, e.g., 3 to 300 ms;

ii) LPX: Light Age, Inc.'s Epicare-LPX™, the Alexandrite laser generating the light output at ~755 nm, with average power up to 100 Watts; pulse rate up to 3 Hz; pulse duration from, e.g., 3 to 300 ms;

iii) DUO: Light Age, Inc.'s Epicare-DUO™, the Alexandrite generating the light output at ~755 nm and Nd:YAG laser at 1064 nm, with average power up to 150 Watts; pulse rate from, e.g., 1 to 10 Hz, and pulse duration from, e.g., 0.5 ms (millisecond) to 300 ms; and iv) PAL: Light Age, Inc.'s PAL-101™, the tunable Alexandrite laser from, e.g., 720 to 820 nm, typical power is 10 Watts at 10 Hz; and pulse duration from, e.g., 10 ns (nanosecond) to 10 us (microsecond).

In some embodiments, as shown in FIG. 1, the inventive Tm:YAG systems can be housed in a small enclosure that can perform as an attachment to treatment head of the Alexandrite laser systems such as LP, LPX, or DUO medical system.

The inventive solid-state Tm:YAG system operates based at least in part on the following principles. In some embodiments, when Tm3+ ions are doped into solid-state host crystals (most commonly, YAG), the resulting medium has a strong absorption band around, e.g., 765 to 785 nm, which falls into the emission of Alexandrite lasers. In some embodiments, when pumped by a light of around 785 nm, Tm:YAG laser has a sufficiently high optical conversion efficiency. In some embodiment, the Alexandrite laser systems (e.g., LP, LPX and DUO) are typically designed to lase at fixed wavelength, which is around 755 nm. In some embodiments, the inventive device of the instant invention can shift the typical output of the Alexandrite laser systems to a wavelength of 785 nm. In some embodiments, the inventive laser devices of the instant invention can pump the Tm:YAG medium at wavelength of 755 nm but with a relatively lower efficiency.

In some embodiments, the inventive laser devices of the instant invention can at least partially compensate the relatively lower efficiency of pumping at the wavelength of 755 nm by: i) utilizing a Tm:YAG medium that would be longer in length if the Tm:YAG medium that would be pumped at wavelength of 785 nm, and/or ii) increasing Tm3+ ion concentration. In some embodiments, utilizing a relatively elongated Tm:YAG medium results in improved heat distribution evenly throughout the entire Tm:YAG medium which results in lowering risk of the thermal fracture in the Tm:YAG medium.

In some embodiments, the inventive laser devices of the instant invention utilize the Tm:YAG medium is a form of a rod having 5 mm diameter and being 60 mm long. In some embodiments, the inventive laser devices of the instant invention utilize the Tm:YAG medium doped with 4% of Tm3+ ions. In some embodiments, the inventive laser devices of the instant invention utilize the Tm:YAG medium doped with at least 4% of Tm3+ ions. In some embodiments, the inventive laser devices of the instant invention utilize the Tm:YAG medium doped with 6% of Tm3+ ions. In some embodiments, the inventive laser devices of the instant invention utilize the Tm:YAG medium doped with at least 6% of Tm3+ ions. In some embodiments, the inventive laser devices of the instant invention utilize the Tm:YAG medium doped less than 50% of Tm3+ ions. In some embodiments, the inventive laser devices of the instant invention utilize the Tm:YAG medium doped with less than 25% of Tm3+ ions. In some embodiments, the inventive laser devices of the instant invention utilize the Tm:YAG medium doped with less than 15% of Tm3+ ions. In some embodiments, the inventive laser devices of the instant invention utilize the Tm:YAG medium doped with less than 10% of Tm3+ ions.

In some embodiments, as shown in FIG. 1, the inventive Tm:YAG systems include at least one optical fiber (101) that delivers the output of the Alexandrite laser into at least one Lens system (102) that is designed to collimate the Alexandrite output beam from fiber to the size that is slightly smaller (less than 25% size deviation) than a cross area or a size of the Tm:YAG medium (e.g., the collimated Alexandrite output beam has a diameter that is slightly less than the Tm:YAG rod diameter of 5 mm). In some embodiments, the collimated Alexandrite output beam has a size that is less than 20% size deviation than a cross area or a size of the Tm:YAG medium. In some embodiments, the collimated Alexandrite output beam has a size that is less than 15% size deviation than a cross area or a size of the Tm:YAG medium. In some embodiments, the collimated Alexandrite output beam has a size that is less than 10% size deviation than a cross area or a size of the Tm:YAG medium. In some embodiments, the collimated Alexandrite output beam has a size that is less than 5% size deviation than a cross area or a size of the Tm:YAG medium. In some embodiments, the collimated Alexandrite output beam has a size that is less than 1% size deviation than a cross area or a size of the Tm:YAG medium.

In some embodiments, the Lens system includes at least one lens. In some embodiments, the Lens system includes a plurality of lenses (e.g., at least two, at least three, at least four, etc.). In some embodiments, lenses of the Lens system have spherical shape. In some embodiments, the inventive devices of the instant invention can utilize various number of lenses having various shapes in order to collimate the Alexandrite beam output from the fiber to the size that is about slightly less than the cross section of the Tm:YAG medium that the pumping light impinges (e.g., is about 80% of the Tm:YAG rod diameter.)

In some embodiments, the collimated Alexandrite output beam is directed at the Tm:YAG medium along the longitudinal axis of the Tm:YAG medium. In some embodiments, the collimated Alexandrite output beam is directed at the Tm:YAG medium at a certain angle to the longitudinal axis of the Tm:YAG medium.

In some embodiments, as shown in FIG. 1, a cavity (103) which houses the Tm:YAG medium consists at least of: at least one pump mirror, the Tm:YAG medium, and at least one output coupler. In some embodiments, pump mirror(s)' shape (or curvature) are such to obtain a sufficiently stable cavity which means that light (or photons) can be traveling back and forth between pump mirror and output coupler for many times without significant loss. In some embodiments, the instant invention utilizes at least one or more of the following characteristics to design the cavity:

i) stability; and ii) mode matching with pump laser which ensures that the highest possible energy extraction efficiency.

In some embodiments, the instant invention allows a flexibility in utilizing mirrors of various numbers of mirror having various shapes as long as the above two criteria are met. In some embodiments, the instant invention utilizes the Lascad software program (http://www.las-cad.com) to simulate cavity setup.

In some embodiments, in case of the end pumping scheme is used, the inventive devices of the instant invention utilize pump mirrors that have the mirror reflectivity (e.g., a high reflector is reflecting >99.5% of light at near infrared (e.g., between 1.85 to 2.1 um), and only reflecting <1% of visible pump laser (e.g., between 750 nm to 790 nm). Output coupler can have different reflectivity at near infrared (e.g., between 1.85 to 2.1 um), and has no requirement on reflectivity at visible pump. In some embodiments, the inventive devices of the instant invention utilize pump mirrors having at least 80% reflectivity for, e.g., 1.85-2.1 um.

In some embodiments, the pump mirror is eliminated by coating one Tm:YAG rod end with the desired mirror reflectivity (e.g., a high reflector is reflecting >99.5% of light at near infrared (e.g., between 1.85 to 2.1 um), and only reflecting <1% of visible pump laser (e.g., between 750 nm to 790 nm). In some embodiments, the output coupler is eliminated by coating one Tm:YAG rod end with the desired reflectivity at near infrared (e.g., between 1.85 to 2.1 um), and no requirement on reflectivity at visible pump. In some embodiments, both pump mirror and output coupler are eliminated by one Tm:YAG rod end coated with mirror reflectivity (e.g., a high reflector is reflecting >99.5% of light at near infrared (e.g., between 1.85 to 2.1 um), and only reflecting <1% of visible pump laser (e.g., between 750 nm to 790 nm) and the other end of Tm:YAG rod coated with the desired reflectivity at near infrared (e.g., between 1.85 to 2.1 um), and no requirement on reflectivity at visible pump.

In some embodiments, the inventive devices of the instant invention utilize output couplers having at least 50% reflectivity for, e.g., 1.85-2.1 um. In some embodiments, the inventive devices of the instant invention utilize pump mirrors having at least 85% reflectivity for, e.g., 1.85-2.1 um. In some embodiments, the inventive devices of the instant invention utilize pump mirrors having at least 95% reflectivity for, e.g., 1.85-2.1 um. In some embodiments, the inventive devices of the instant invention utilize pump mirrors having at least 99% reflectivity for, e.g., 1.85-2.1 um.

In some embodiments, as shown in FIG. 1, the Tm:YAG output from the cavity passes through at least one dichroic glass (104) that is utilized to reject residue at 755 nm, and allow to obtain the desired output of the inventive devices. In some embodiments, the desired output of the inventive devices is a beam having a wavelength of 2 micron.

Figure 2:
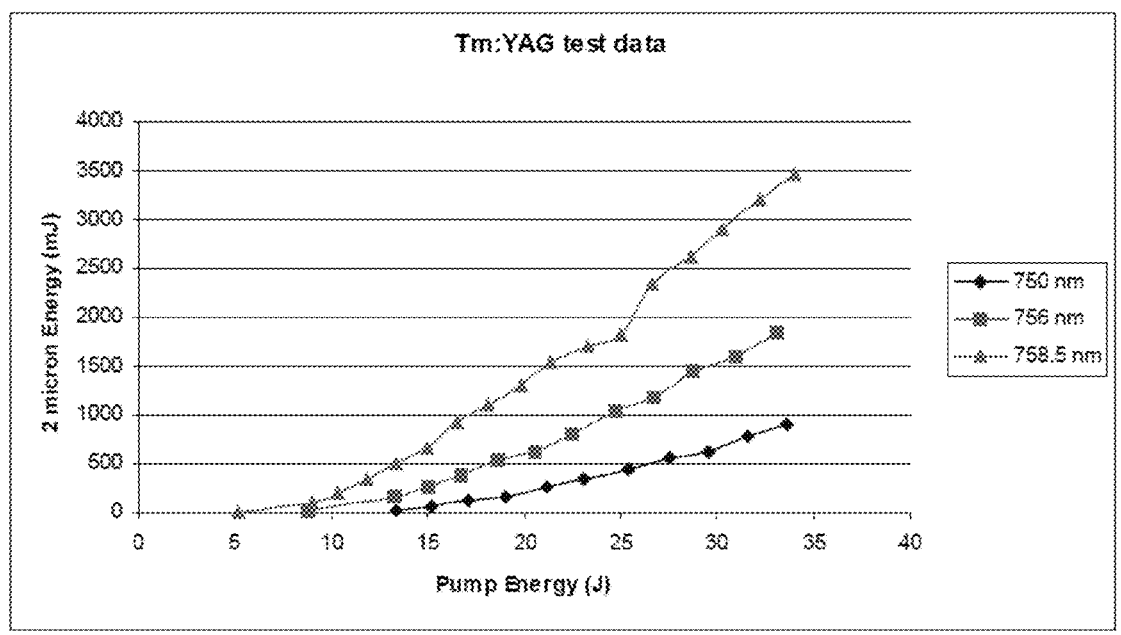
FIG. 2 illustrates some embodiments of the present invention.

FIG. 2 shows the measured 2 micron output energy of the Tm:YAG laser in some embodiments of the instant invention as a function of the measured pumping energy of the Alexandrite laser with different wavelength around 755 nm. In same embodiments, the following operation conditions of the Alexandrite laser resulted in the following output energy of Tm:YAG:

i) Alexandrite laser output of 750 nm output at 3 ms durations resulted in the Tm:YAG output of up to 3 J at 2 um;

ii) Alexandrite laser output of 755 nm output at 3 ms durations resulted in the Tm:YAG output of up to 5 J at 2 um;

iii) Alexandrite laser output of 758 nm output at 3 ms durations resulted in the Tm:YAG output of up to 10 J at 2 um; and iv) Alexandrite laser output of, e.g., 750-760 nm output at 10 ms or longer durations resulted in the Tm:YAG output of less than 1 J at 2 um.

In some embodiments, the small wavelength adjustment of the Alexandrite laser output was obtained by utilizing different output coupler(s) in the LPX Alexandrite laser system, without mechanically or electrically modification to the LPX Alexandrite laser system. In FIG. 2, all other parameters, such as Tm:YAG concentration, rod dimension, and the output coupler's reflectivity, were the same.

As FIG. 2 illustrates, the output energy of the Tm:YAG laser systems of the instant invention is sufficiently high because the Alexandrite output is sufficiently closer to the peak absorption of Tm:YAG material. In same embodiments, the output energy of the Tm:YAG laser systems of the instant invention is sufficiently high because the Alexandrite output has the pumping pulse duration of 3 ms which matches the lifetime of Tm:YAG material (10 ms nominally). In same embodiments, the output energy of the Tm:YAG laser systems of the instant invention is sufficiently high because the Alexandrite output produces more than 40 Joules pumping energy.

In some embodiments, the gain of Tm:YAG material depends on temperature, and generally decreases as the temperature of Tm:YAG material increases due to an increase in up conversion rate. In some embodiments, when the Tm:YAG material is pumped by Alexandrite laser, an estimated amount of 25% of energy absorbed by the Tm:YAG material is transferred into heat, which in turn will raise the temperature of the Tm:YAG material. In some embodiments, at a pumping rate of 40 W, the heat produced is about 10 W, and is distributed through the whole length of the Tm:YAG material. In some embodiments, at least one thermal-electric cooler (TEC) can be used to remove the heat and stabilize the temperature of the Tm:YAG material. In some embodiments, instead of using TEC, the inventive laser systems of the instant invention can utilize designs (e.g., designs with chillers) that supply airflows from cold air chillers to cool the Tm:YAG material.

In some embodiments, the inventive laser systems of the instant invention can be utilized in dermatologic surgeries to perform medical treatments such as, but not limited to:

i) fractional resurfacing of facial actinic keratoses;
ii) treatment of non-facial photo damage;
iii) treatment of actinic cheilitis;
iv) treatment of macular seborrheic keratoses;
v) treatment of melisma cheilitis; and
vi) remove facial wrinkles.

In some embodiments, the inventive laser systems of the instant invention can be utilized in light detection and ranging (LIDAR), such as Coherent Doppler wind detection.

In some embodiments, the inventive laser systems of the instant invention can be utilized in laser radar systems.

Figure 3:
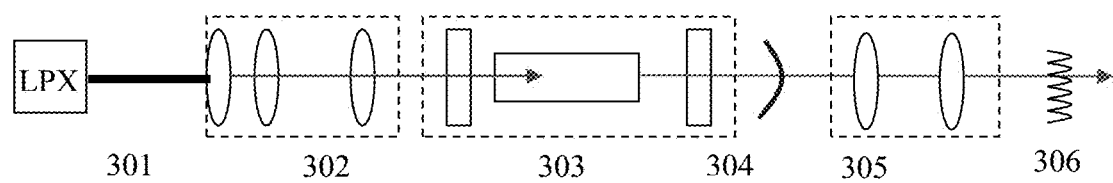
FIG. 3 illustrates some embodiments of the present invention.

FIG. 3 illustrates principle of laser cavity design in according to some embodiments of the instant invention, which is similar as the one shown in FIG. 1 but differs from FIG. 1 in part that the dichroic mirror (304) is designed to reflect back onto Tm:YAG rod. In some embodiments, the design of FIG. 3 can enhance the Tm:YAG laser output by at least 20%. In some embodiments, the inventive laser device of the instant invention can employ an output lens system (305) to expand the beam size of Tm:YAG cavity output, and/or a microlens array system that gives fractional output suitable for, for example but is not limited to, medical applications. In FIG. 3, the following numbers represent specific parts of the instant invention: 301 (optical fiber), 302 (input lenses), 303 (cavity), 304 (dichroic glass), 305 (output lenses), and 306 (micro-lens array).

In some embodiments, the inventive laser device of the instant invention can employ an air integrator that diverts small part of the cooled air from chiller (mainly used for patient comfort in aesthetic procedures) to thermally cool the Tm:YAG rod. In some embodiments, by assembling a Tm:YAG cavity into the air integrator, an exemplary Tm:YAG handpiece of the instant invention can be integrated into various devices such as, but is not limited to, Light Age aesthetic products, such as EpiCare™ LP, LPX and DUO.

Figure 4:
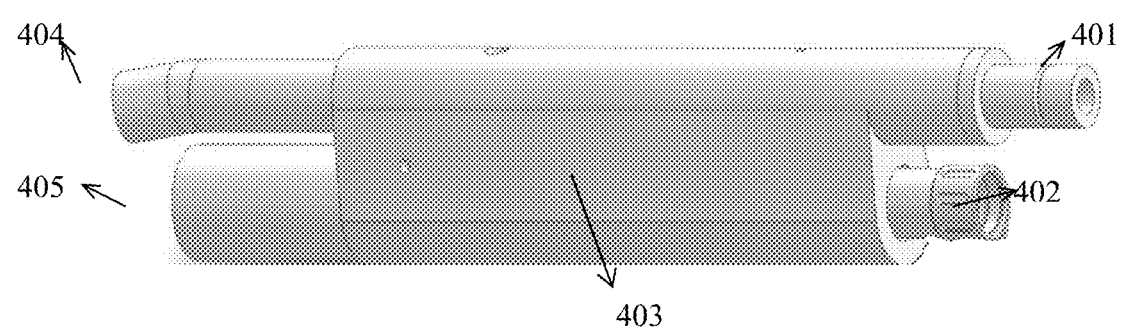
FIG. 4 illustrates another embodiment of the present invention.

FIG. 4 illustrates Tm:YAG handpiece assembly view in accordance with some exemplary embodiments of the instant invention:

1. air input adapter (401);
2. fiber input adapter (402);
3. air integrator (403);
4. air output/air guide (404); and
5. Tm:YAG output (405).

Figure 5:
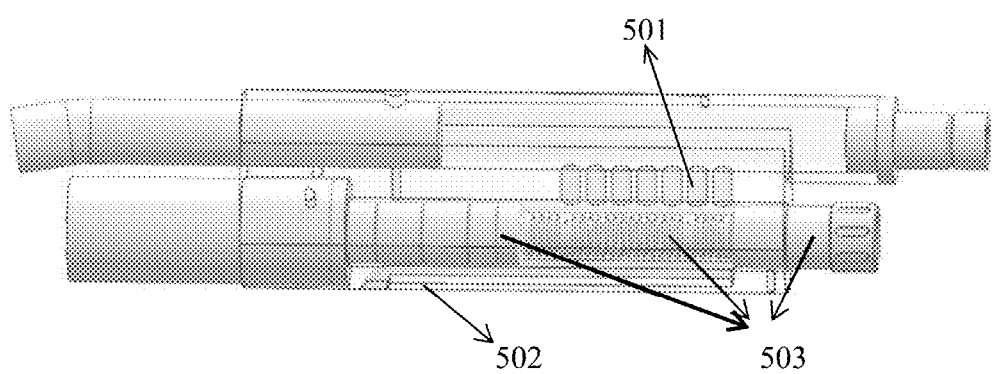
FIG. 5 illustrates yet another embodiment of the present invention.

FIG. 5 illustrates an air integrator sectional view in accordance with some exemplary embodiments of the instant invention:

1. air channels (501);
2. air exhaust hole (502); and
3. Tm:YAG cavity (503).

Figure 6:
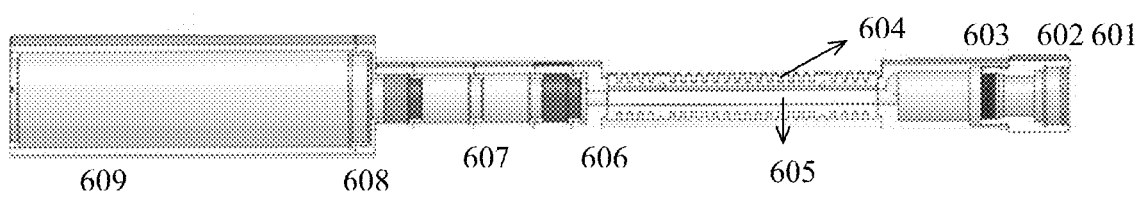
FIG. 6 illustrates another embodiment of the present invention.

FIG. 6 illustrates a Tm:YAG cavity sectional view in accordance with some exemplary embodiments of the instant invention:

1. fiber input adapter (601);
2. input lenses (602);
3. pump mirror (603);
4. rod heat sink (604);
5. Tm:YAG rod (605);
6. output coupler (606);
7. Dichroic (607);
8. output lenses (608); and
9. micro-lens array (609)

Figure 7:
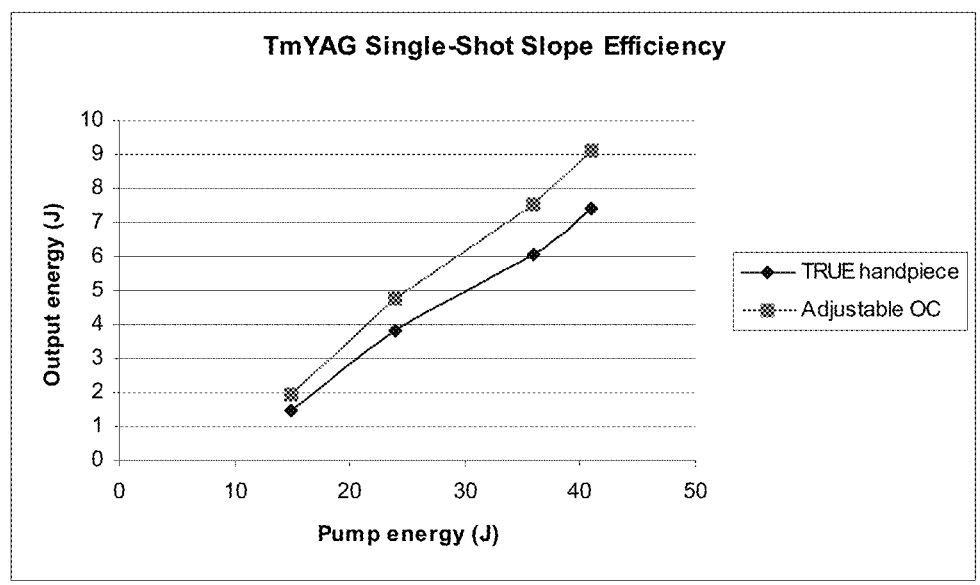
FIG. 7 illustrates some embodiments of the present invention.

Test Data of an Exemplary Tm:YAG Handpiece in Accordance with Some Exemplary Embodiments of the Instant Invention Slope Efficiency FIG. 7 illustrates the slope efficiency of Tm:YAG output at ~2 micron, with comparison of a handpiece setup (marked as "TRUE handpiece") and a laboratory setup (marked as "adjustable OC") in accordance with the some embodiments of the instant invention. The setups were pumped by 756 nm output from LightAge's EpiCare™ LPX unit with 3 ms pulse duration settings. In some embodiments, the latter allows the output coupler to be adjusted so that the cavity alignment is optimized, while no such adjustment is in the TRUE handpiece.

Tm:YAG Output without Cooling

Figure 8:
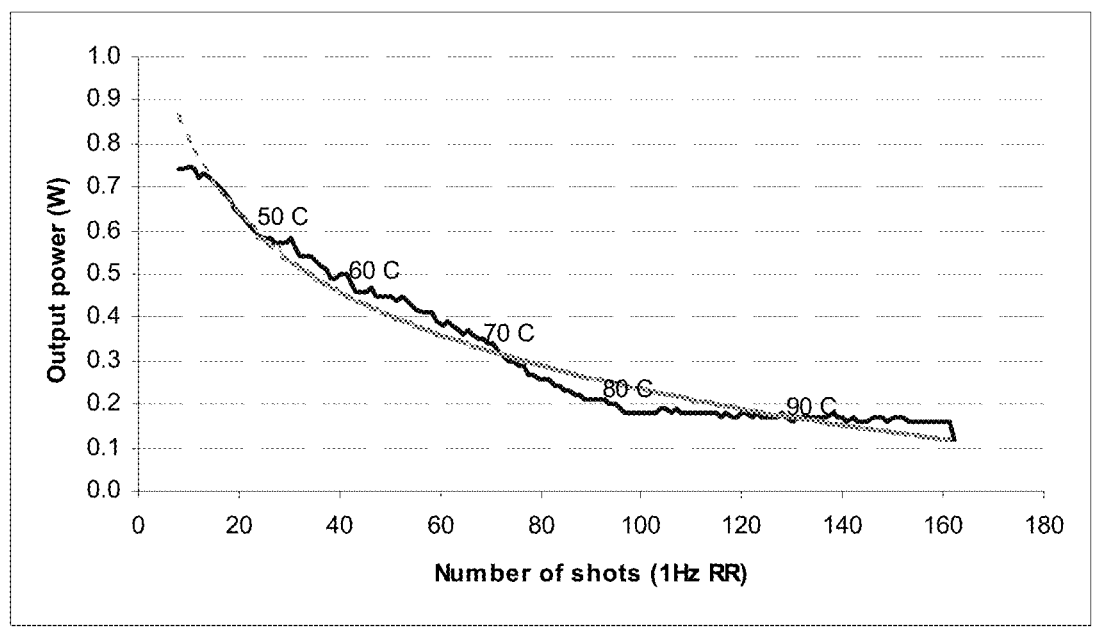
FIG. 8 further illustrates some embodiments of the present invention.

FIG. 8 illustrates the output power drop from Tm:YAG handpiece when no cooling is present. FIG. 8 also shows the estimated temperature of rod on the figure. The gray line is a logarithmic fit. The pumping energy is about 15 J. Thus, in some embodiments, the instant invention utilizes cooling in Tm:YAG handpiece design.

Tm:YAG Output (without Microlens Array)

Figure 9:
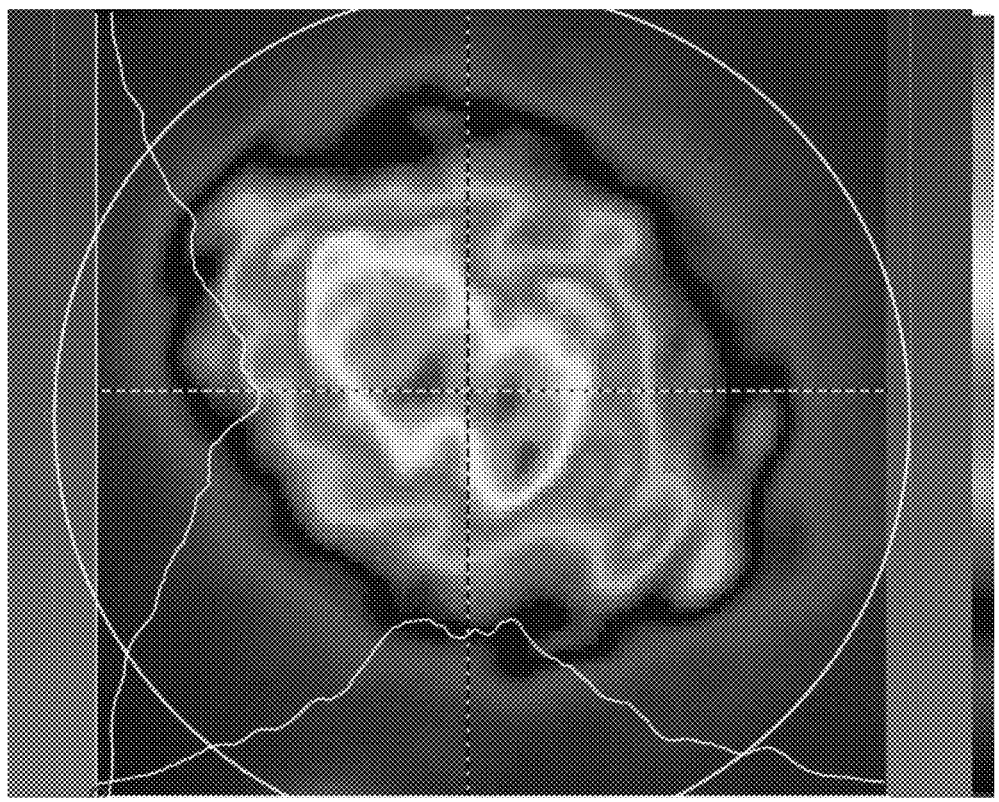
FIG. 9 still further illustrates some embodiments of the present invention.

FIG. 9 illustrates a near field image of the Tm:YAG handpiece output. In this specific example, the beam quality ($M^2$ factor) of the output is about 30.

Tm:YAG Fractional Output (with Microlens Array)

Figure 10:
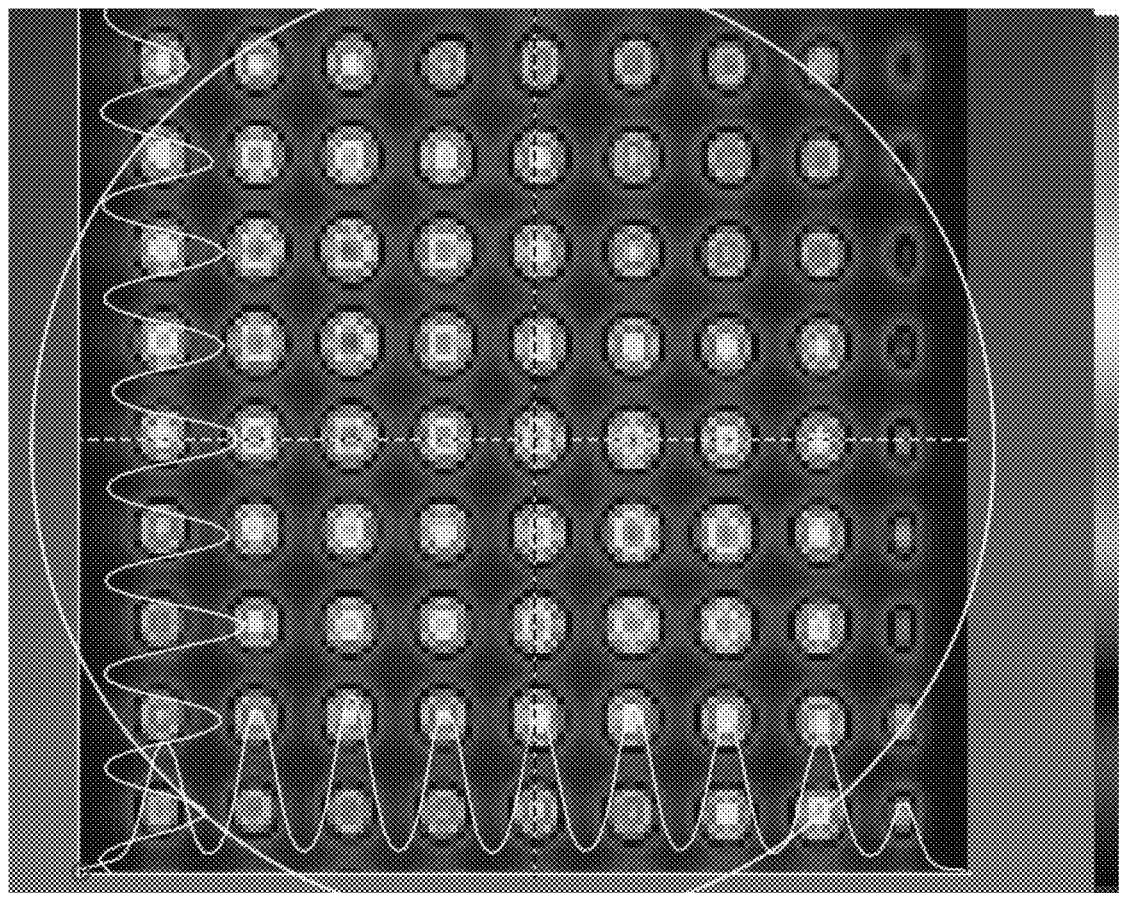
FIG. 10 illustrates some embodiments of the present invention.

FIG. 10 illustrates an image of output from Tm:YAG handpiece equipped with micro-lens array. In accordance with some embodiments, the micro-lens array in this particular setup of FIG. 10 has, but is not limited to, 1000 micron pitch with 6.1 cm focal length, and a size of an individual spot is roughly 400 microns. In some embodiments, a microlens array for producing fractional output can be utilized for various dermatology treatments.

In some embodiments, the instant invention can employ various lens array (varied in pitch size and focal length) to form various patterns. In some embodiments, the instant invention can rely on the pitch and focal length of micro-lens array to determine factors, such as but are not limited to: the spot size of each fractional spot and the fill factor (the ratio between area covered by illumination and total treatment area). In some embodiments, the spot size of each fractional spot and the fill factor can affect the efficiency and/or efficacy in patient treatment. For example, in some embodiments, the instant invention employ a lens array that results in the spot size around 360 microns and fill factor of 10%.

In some embodiments, for example, the spot size of each fractional spot and the fill factor can be determined as discussed in Polder K D, Bruce S., *Treatment of melasma using a novel 1,927 nm fractional thulium fiber laser: A pilot study.*, Dermatologic Surgery, 2012 (38:199-206), whose the specific disclosures related to the spot size of fractional spots, the fill factor, the effectiveness and side effects of 1927 nm thulium device on the treatment of melasma are hereby incorporated herein by reference for such specific purposes. Specifically, patients were subjected to three to four treatment sessions at 4 week intervals, and each treatment utilized different/distinct spot sizes and fill factors.

Temporal Profile of Tm:YAG Output

Figure 11:
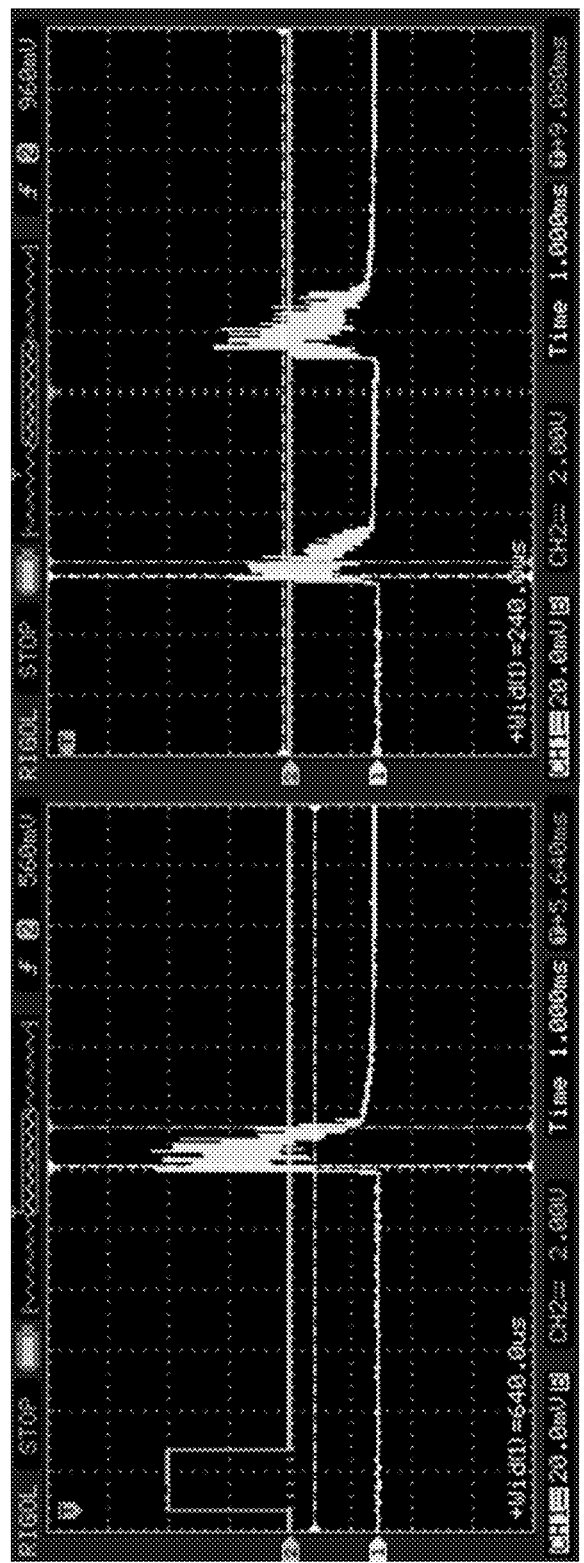
FIG. 11 also illustrates some embodiments of the present invention.

FIG. 11 illustrates an exemplary temporal profile of Tm:YAG output. In FIG. 11, the left panel shows output under S-mode, and the right panel shows output under 3-ms mode. For FIG. 11, a semiconductor photodetector (rise time less than 1 ns) was employed to measure the temporal shape of Tm:YAG output, pumped at two different settings by LightAge's EpiCare™ LPX. In FIG. 11, the horizontal scale (time) in oscilloscope settings is 1 ms/division. FIG. 11 shows that, in some embodiments, the pulse duration is about 0.64 ms when pumped in S-mode, and is about, e.g., 3.5 to 4 ms (two-pulse structure) when pumped in 3-ms mode.

Long-Term Stability Test

Figure 12:
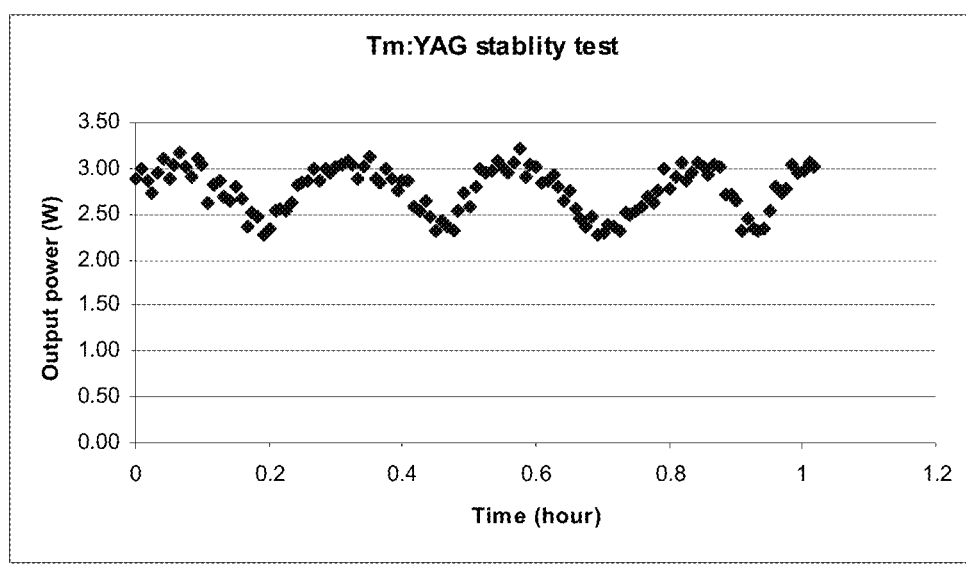
FIG. 12 illustrates some embodiments of the present invention.

FIG. 12 illustrates the output stability of Tm:YAG handpiece by continuously pumping, at the repetition rate of 1 Hz, the Tm:YAG handpiece over a period of one hour, with cooling air is on (see FIG. 8 for performance without cooling). The output power is logged on a power meter, and plotted in FIG. 12. In some embodiments, a 15-minute period oscillation is not critical to the intended operation in accordance with the principals of the instant invention. In some embodiments, the period oscillation can be affected by the thermal effect in the pump laser and/or the output from a chiller.

Tm:YAG Handpiece Output Wavelength

Figure 13:
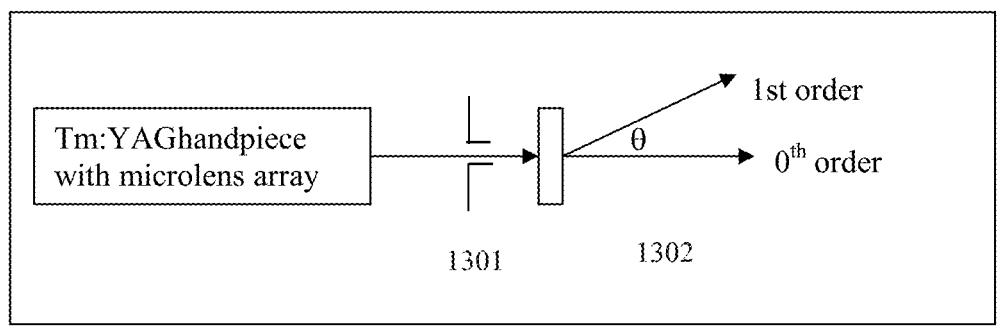
FIG. 13 further illustrates some embodiments of the present invention.

FIG. 13 illustrates the measurement of output wavelength in the exemplary setup. For some embodiments, the angle θ between 1st order (deflected beam) and un-deflected beam (0th order) is measured to be 35.75 degrees. The wavelength measurement was taken by using commercial grating, as shown in FIG. 13. The measured wavelength is 1.96 microns, derived from the grating's equation, with 0.04 microns resolution.

In some embodiments, as shown in FIG. 13, the inventive systems of the instant invention may not include a wavelength limiting/selecting device, which can be added depending on a specific application based on desirability for having wavelength(s) between, e.g., 1.75 um and to 2.1 um. In accordance with FIG. 13, the output wavelength then is determined by the peak gain of Tm:YAG material and the peak location of HR/OC reflectivities. The aperture (1301) and grating at 300 lines/mm (1302) are identified in FIG. 13.

In some embodiments, the instant invention provides for a system that includes at least the following components: (i) an Alexandrite laser pumping subsystem; where the Alexandrite laser pumping subsystem is configured to: 1) produce wavelengths between 700 and 820 nm, and 2) produce a pump pulse having: i) a duration between 1 to 10 milliseconds, and ii) an energy measuring up to 100 Joules; where the Alexandrite laser pumping subsystem includes: 1) at least one optical fiber, and 2) at least one Lens system, where the at least one optical fiber is configured to deliver an Alexandrite output beam of an Alexandrite gain medium into the at least one Lens system; (ii) a Thulium doped Yttrium Aluminum Garnet (Tm:YAG) laser subsystem; where the Tm:YAG laser subsystem includes: 1) a Tm:YAG gain medium; where a Tm:YAG gain medium of the Tm:YAG laser subsystem is optically pumped by the Alexandrite laser pumping subsystem; where the Tm:YAG gain medium is doped with Tm3+ ions to a concentration of between 1% and 50% Tm3+ ions; and where the at least one Lens system is configured to collimate the Alexandrite output beam from the at least one optical fiber to a size that is smaller than a diameter of the Tm:YAG gain medium; 2) a rod heat sink, where the rod heat sink encases the Tm:YAG gain medium; and 3) at least one cooling device, where the at least one cooling device is configured to stabilize the temperature of the Tm:YAG gain medium; (iii) a wavelength selecting device, where the wavelength selecting device is configured to deliver a wavelength between 1.75 microns to 2.1 microns; and where the system is configured to produce a high energy conversion efficiency at: 1) multi-Joule-Level pulse energies and 2) multi-Watt Level average powers.

In some embodiments, the Alexandrite laser pumping subsystem further includes: (i) a fiber input adapter and (ii) at least one input lens, where the at least one input lens is encased in the fiber input adapter.

In some embodiments, the Tm:YAG laser subsystem further includes: (i) a rod heat sink, where the rod heat sink is directly contacting the fiber input adapter; (ii) a high reflector, where the high reflector is encased in the fiber input adapter and is optically contacting with the at least one input lens; (iii) at least one output coupler, where the at least one output coupler is directly contacting the heat rod sink; (iv) a dichroic glass, where the dichroic glass is optically contacting the at least one output coupler; and (v) at least one output lens, where the at least one output lens is optically contacting the dichroic glass.

In some embodiments, the system further includes a micro-lens array, where the micro-lens array is configured to form a pattern, where the pattern is determined by a pitch and a focal length of the micro-lens array; and where the micro-lens array is optically contacting the at least one output lens.

In some embodiments, the system further includes: a compact Thulium ion-based wavelength convertor configured to fit into a handpiece, where the handpiece includes: (i) an air input adapter, (ii) a fiber input adapter, (iii) an air integrator, (iv) an air output/air guide, and (v) a Tm:YAG output.

In some embodiments, the Alexandrite laser pumping subsystem is configured to use cold airflow to remove heat from the Tm:YAG laser subsystem.

In some embodiments, the system is utilized for a dermatologic surgery, where the dermatologic surgery is selected from the group consisting of: fractional resurfacing of facial actinic keratosis, treatment of non-facial photo damage, treatment of actinic cheilitis, treatment of macular seborrheic keratosis, treatment of melisma cheilitis, and treatment by removal of facial wrinkles.

In some embodiments, the Alexandrite output beam measuring between 750-760 nm and an output energy measuring between 1 ms-10 ms durations results in a Tm:YAG output measuring between 1 J-10 J at 2 microns.

In some embodiments, the Alexandrite output beam is configured to be delivered at a wavelength of 755 nm.

In some embodiments, the micro-lens array is configured to generate a spot size of about 360 microns and a fill factor of about 10%.

In some embodiments, the Tm:YAG gain medium is in a form of a rod measuring 5 mm in diameter and 60 mm in length.

In some embodiments, the system further includes: a cavity configured to encase at least one pump mirror, the Tm:YAG gain medium, and the at least one output coupler.

In some embodiments, the at least one pump mirror is configured to achieve at least 80% reflectivity for 1.85-2.1 um.

In some embodiments, the instant invention provides for a method that includes at least the following steps: (i) utilizing an Alexandrite laser pumping subsystem; where the Alexandrite laser pumping subsystem is configured to: 1) produce wavelengths between 700 and 820 nm, and 2) produce a pump pulse having: i) a duration between 1 to 10 milliseconds, and ii) an energy measuring up to 100 Joules; where the Alexandrite laser pumping subsystem includes: 1) at least one optical fiber, and 2) at least one Lens system, where the at least one optical fiber is configured to deliver an Alexandrite output beam of an Alexandrite gain medium into the at least one Lens system; (ii) utilizing a Thulium doped Yttrium Aluminum Garnet (Tm:YAG) laser subsystem; where the Tm:YAG laser subsystem includes: 1) a Tm:YAG gain medium; where a Tm:YAG gain medium of the Tm:YAG laser subsystem is optically pumped by the Alexandrite laser pumping subsystem; where the Tm:YAG gain medium is doped with Tm3+ ions to a concentration of between 1% and 50% Tm3+ ions; and where the at least one Lens system is configured to collimate the Alexandrite output beam from the at least one optical fiber to a size that is smaller than a diameter of the Tm:YAG gain medium; 2) a rod heat sink, where the rod heat sink encases the Tm:YAG gain medium; and 3) at least one cooling device, where the at least one cooling device is configured to stabilize the temperature of the Tm:YAG gain medium; (iii) utilizing a wavelength selecting device, where the wavelength selecting device is configured to deliver a wavelength between 1.75 microns to 2.1 microns; and where the system is configured to produce a high energy conversion efficiency at: 1) multi-Joule-Level pulse energies and 2) multi-Watt Level average powers.

While a number of embodiments of the present invention have been described, it is understood that these embodiments are illustrative only, and not restrictive, and that many modifications may become apparent to those of ordinary skill in the art. Further, while the disclosure herein identifies specific applications of the inventive laser systems, it is understood that those specific application are merely illustrative and are not limiting. Specifically, as detailed above, in at least some embodiments, the instant invention is generally directed to any solid-state laser system in which the Alexandrite laser is utilized as the pumping source.

What is claimed is:
1. A system comprising:
 (i) a first laser pumping subsystem, wherein the first laser pumping subsystem is alexandrite gain medium and is configured to:
  1) produce a pump pulse having wavelengths between 700 and 820 nm, and
  2) said pump pulse having:
   i) a duration between 1 to 100 milliseconds, and
   ii) an energy measuring between 1 and 100 Joules;
 (ii) a pump pulse delivery subsystem comprising:
  1) at least one optical fiber, and
  2) one or more optional pulse conditioning optics,
  wherein the at least one optical fiber is configured to deliver an alexandrite pump pulse into the optional conditioning optics which may include a focusing element such as a lens for conveyance into a second pumped laser subsystem incorporating a Thulium (Tm) ion containing gain medium,
  wherein the second pumped laser subsystem consists of an optical resonator comprising: a Thulium ion containing gain medium such as Tm:YAG or other materials including, but are not limited to, Tm containing glass, YALO and ZBLAN hosts or co-doped materials such as Tm:Ho:YAG,
  wherein the optical resonator consists of mirrors coated to reflect light at the desired lasing wavelength, such mirrors may be separate from or coated onto a pumped laser gain medium and wherein such resonator permits the light from the pump pulse to enter the pumped laser gain medium by means of, for example, a dichroic optic having substantial transmission at the wavelength of the pump pulse and substantial reflection at a pumped laser output wavelength or having substantial reflection at wavelength of the pump pulse and substantial transmission at the pumped laser output wavelength, or by use of a dispersive optics to bring the pump pulse into reasonable spatial alignment with the axis of a pumped laser resonator.

2. The System of claim 1, wherein the gain medium is Tm:YAG and the Tm:YAG gain medium is doped with Tm3+ ions to a concentration of between 1 and 50 atomic percent.

3. The System of claim 1, wherein the pulse conditioning optics are configured to collimate the pump pulse from the at least one optical fiber to a size that is smaller than a diameter of the Tm:YAG gain medium.

4. The system of claim 3, wherein the diameter of Tm gain medium is between 1 mm and 10 mm and the pump pulse impinging on the Tm gain medium is between 0.1 mm and 9 mm.

5. The laser systems of claim 1, wherein the laser gain medium is in thermal contact with a heat removal system, such heat removal system consisting of a static of flowing liquid or a thermally conductive solid material ("heat sink").

6. The laser system of claim 5, wherein the liquid is water.

7. The laser system of claim 5, wherein the conductive solid material is a metal such as copper, gold or aluminum or nonmetallic thermally conductive material such as sapphire or undoped YAG.

8. The laser system of claim 5, wherein a cooling device such as a thermo electric cooling element of elements (TECs) or a cold air chiller is used to stabilize the temperature of the heat sink.

9. The laser system of claim 1, wherein the pumped laser resonator additionally incorporates a wavelength selecting device, and wherein the wavelength selecting device is configured to permit lassing at one or more selected wavelengths between 1.75 microns to 2.1 microns.

10. The system of claim 1, wherein the first laser pumping subsystem further comprises:
    (i) a fiber input adapter; and
    (ii) at least one input lens, wherein the at least one input lens is encased in the fiber input adapter.

11. The system of claim 1, wherein the Tm:YAG laser subsystem further comprises:
    (i) a rod heat sink, wherein the rod heat sink is directly contacting the fiber input adapter;
    (ii) a high reflector, wherein the high reflector is encased in the fiber input adapter and is optically contacting with the at least one input lens;
    (iii) at least one output coupler, wherein the at least one output coupler is directly contacting the heat rod sink;
    (iv) a dichroic glass, wherein the dichroic glass is optically contacting the at least one output coupler; and
    (v) at least one output lens, wherein the at least one output lens is optically contacting the dichroic glass.

12. The system of claim 1, further comprising a micro-lens array,
wherein the micro-lens array is configured to form a pattern,
wherein the pattern is determined by a pitch and a focal length of the micro-lens array, and
wherein the micro-lens array is optically contacting the at least one output lens.

13. The system of claim 1, further comprising:
a compact Thulium ion-based wavelength convertor configured to fit into a handpiece,
wherein the handpiece comprises:
    (i) an air input adapter,
    (ii) a fiber input adapter,
    (iii) an air integrator,
    (iv) an air output/air guide, and
    (v) output beam conditioning optics.

14. The system of claim 1, wherein the first laser pumping subsystem is configured to use cold airflow to remove heat from the Tm:YAG laser subsystem.

15. The system of claim 1, wherein the system is utilized for a dermatologic surgery, wherein the dermatologic surgery is selected from the group consisting of: fractional resurfacing of facial actinic keratosis, treatment of non-facial photo damage, treatment of actinic cheilitis, treatment of macular seborrheic keratosis, treatment of melisma cheilitis, and treatment by removal of facial wrinkles.

16. The system of claim 1, wherein the Alexandrite output beam measuring between 750-760 nm and an output energy measuring between 1 ms-10 ms durations results in a Tm:YAG output measuring between 1 J-10 J at 2 microns.

17. The system of claim 16, wherein the Alexandrite output beam is configured to be delivered at a wavelength of 755 nm.

18. The system of claim 12, wherein the micro-lens array is configured to generate a spot size of about 360 microns and a fill factor of about 10%.

19. The system of claim 13, further comprising:
a cavity configured to encase at least one pump mirror, the Tm:YAG gain medium, and the at least one output coupler.

20. The system of claim 19, wherein the at least one pump mirror is configured to achieve at least 80% reflectivity for 1.85-2.1 um.

* * * * *